United States Patent
Vitt

(10) Patent No.: US 6,552,351 B2
(45) Date of Patent: Apr. 22, 2003

(54) DEVICE FOR THE DEGERMINATION OF A FLUID BY MEANS OF ULTRAVIOLET RAYS

(76) Inventor: Wolfgang Vitt, Brachwiese 1, D-65252 Taunusstein (DE)

( * ) Notice: Subject to any disclaimer, the term of this patent is extended or adjusted under 35 U.S.C. 154(b) by 0 days.

(21) Appl. No.: 10/198,126

(22) Filed: Jul. 19, 2002

(65) Prior Publication Data

US 2002/0171043 A1 Nov. 21, 2002

Related U.S. Application Data

(63) Continuation of application No. 09/482,057, filed on Jan. 13, 2000, now abandoned.

(51) Int. Cl.⁷ .............................. C02B 1/38; B01J 19/08
(52) U.S. Cl. ................... 250/435; 422/186.04; 210/748
(58) Field of Search ..................... 250/435; 210/186.04, 210/63, 748

(56) References Cited

U.S. PATENT DOCUMENTS

| | | | |
|---|---|---|---|
| 3,926,556 A | * 12/1975 | Boucher | |
| 4,141,830 A | * 2/1979 | Last | |
| 4,230,571 A | * 10/1980 | Dadd | |
| 5,474,748 A | * 12/1995 | Szabo | 422/186.04 |
| 5,547,590 A | * 8/1996 | Szabo | 210/748 |
| 5,753,106 A | * 5/1998 | Schenck | 210/96.1 |
| 6,267,895 B1 | * 7/2001 | Engelhard et al. | 210/748 |

FOREIGN PATENT DOCUMENTS

DE  196 17 467 A1  11/1997

* cited by examiner

Primary Examiner—John R. Lee
Assistant Examiner—Anthony Quash
(74) Attorney, Agent, or Firm—Fulbright & Jaworski, LLP

(57) ABSTRACT

A device for the degermination of a fluid by means of UV rays is arranged such that simultaneously produces ozone for the improvement of the degermination effectiveness.

8 Claims, 2 Drawing Sheets

DEVICE FOR THE DEGERMINATION OF A FLUID BY MEANS OF ULTRAVIOLET RAYS

This application is a continuation application and claims benefit under 35 USC 120 of and incorporates herein by reference, in its entirety, U.S. patent application ser. No. 09/482,057, filed on Jan. 13, 2000, which is now abandoned.

BACKGROUND AND SUMMARY OF THE INVENTION

1. Field of the Invention

The invention deals with a device for degermination of fluid by means of ultraviolet radiation. The device comprises a tube permeable for electromagnetic waves through which the fluid is piped and a case encircling the tube in which at least one ultraviolet radiator is placed.

2. Background of the Invention

DE-OS 196 17 487 discloses a device for the degermination of water, wherein water flows through a quartz glass tube and an UV-C radiator is placed in the headspace of a casing. Due to the high degree of reflection, the casing of the UV-radiator is made of aluminum, or alternatively coated with aluminum color.

In order to obtain a high degermination effect the registered utility model 298 02771.2 provides a device for the degermination of fluids by means of UV-rays wherein sensors recognize fluctuations of the radiation performance. Thus, counter measures can be carried out to correct such fluctuations. This also helps to achieve a high degree of uniformity in the degermination process.

SUMMARY OF THE INVENTION

The invention is meant to solve the task of obtaining both a further improvement of the quality and a better purification of the fluid.

The device mentioned earlier guarantees that the electromagnetic waves of one or several UV-C-radiators not only lay in the tissue destructive range of 254.7 nm but also in the ozone producing range below 200 nm, preferably below 180 nm. Depending on the wave range of the radiation either a quartz glass tube or a tube of other appropriate material is used as the circulatory tube. Appropriate radiators as well as quartz glass tubes for the production of ozone are available on the market.

For the permanent production and inflow of produced ozone to the fluid, an inlet nozzle is fixed to the outside of the casing box for the inflow of filtered air into the casing. The ozone produced in the casing is added to the fluid by means of an inlet nozzle. Seen from the flow direction, the fluid enters the tube through the lower bushing. There are other inflow places possible. However, this arrangement enables the ozone to become effective in the radiation area of the radiators.

Preferably the device is placed such that the fluid flows through the tube horizontally from bottom to top. Thus, the inlet nozzle is fixed in the lower part of the casing box, the side wall of which consists of a metal tube.

In order to effect the blow-by of the ozone into the fluid, the air-pressure in the casing box is higher than the pressure of the fluid in the fluid tube. For this an air feed pump can be connected to the inlet nozzle. The air feed pump as well as a usually used air-filter can be of a known make. The inlet nozzle is equipped with a clack valve to avoid a blow-by of the fluid into the casing should a pressure drop take place.

Preferably a metal inlet tube having a mouth connected to the inlet nozzle at the upper interior space of the casing is provided. Since ozone is lighter than air, it gathers in this part of the interior space and gets to the inlet nozzle through the metal inlet tube.

At the discharge muff of the tube carrying the fluid, a gas separator and gas neutralization device are connected for separating and neutralising excess gases and gas mixtures.

The gas separate is extremely simple and inexpensive in its construction. It can be made by a siphon-like tube bend that disposes of a liquid stop valve at its vertex. The liquid stop valve allows the gas mixtures to escape and closes for liquids.

A container activated charcoal neutralizing the gas mixtures, can be used as gas neutralization device.

Thus, the ozone below a wave range of 200 nm being a product UV-radiation of the air is added to the fluid which is subject of UV-radiation by UV radiator. The degermination of the fluid is effected through the UV radiation. The admission of ozone not only effects an additional oxidation of organic compound in the fluid being made innocuous but also a supplementary extinction of virus and bacteria.

DETAILED DESCRIPTION OF THE PREFERRED EMBODIMENTS

Figure 1:
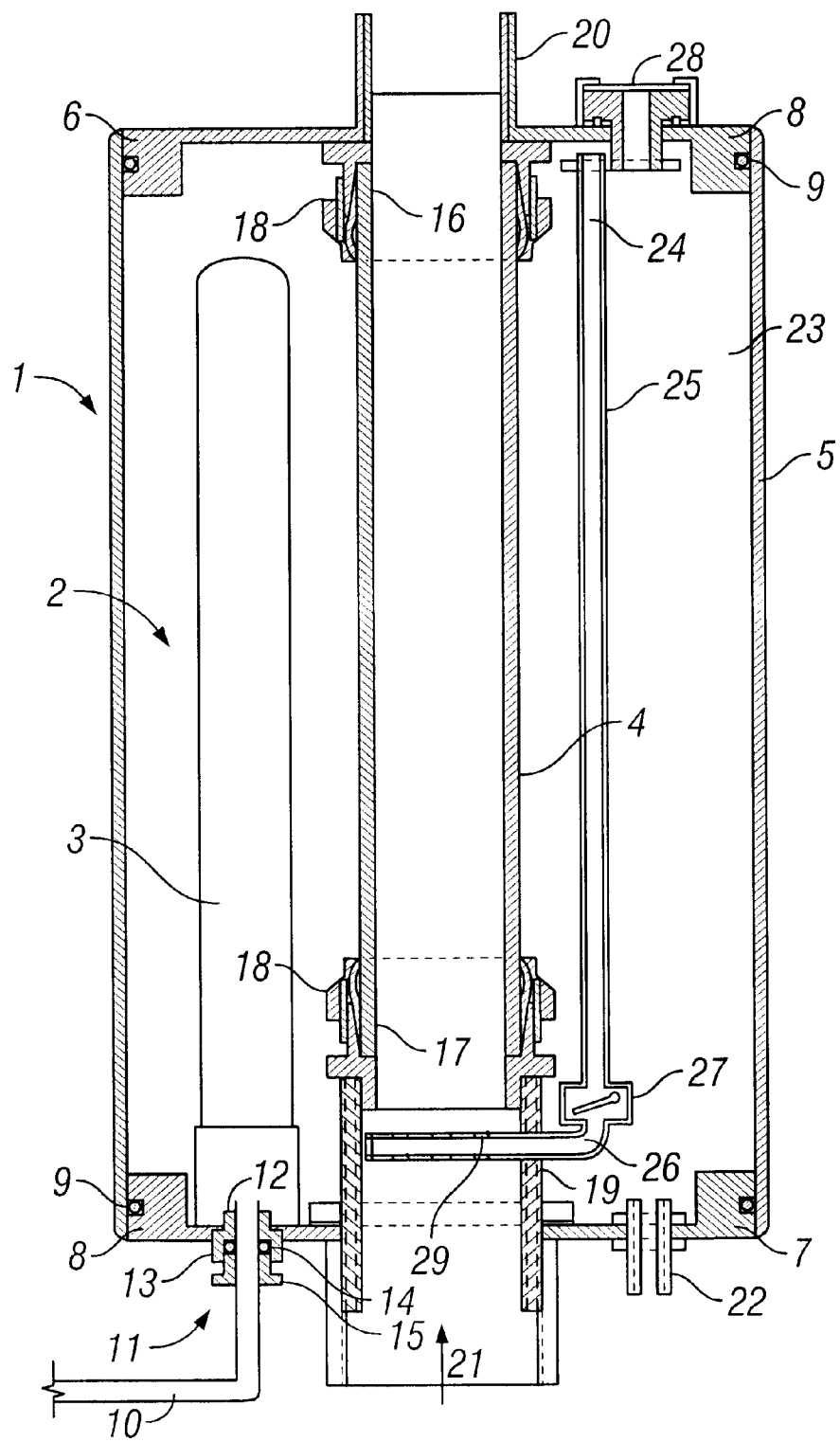
FIG. 1 depicts a cross-sectional view of a degermination device according to the invention.
Figure 2:
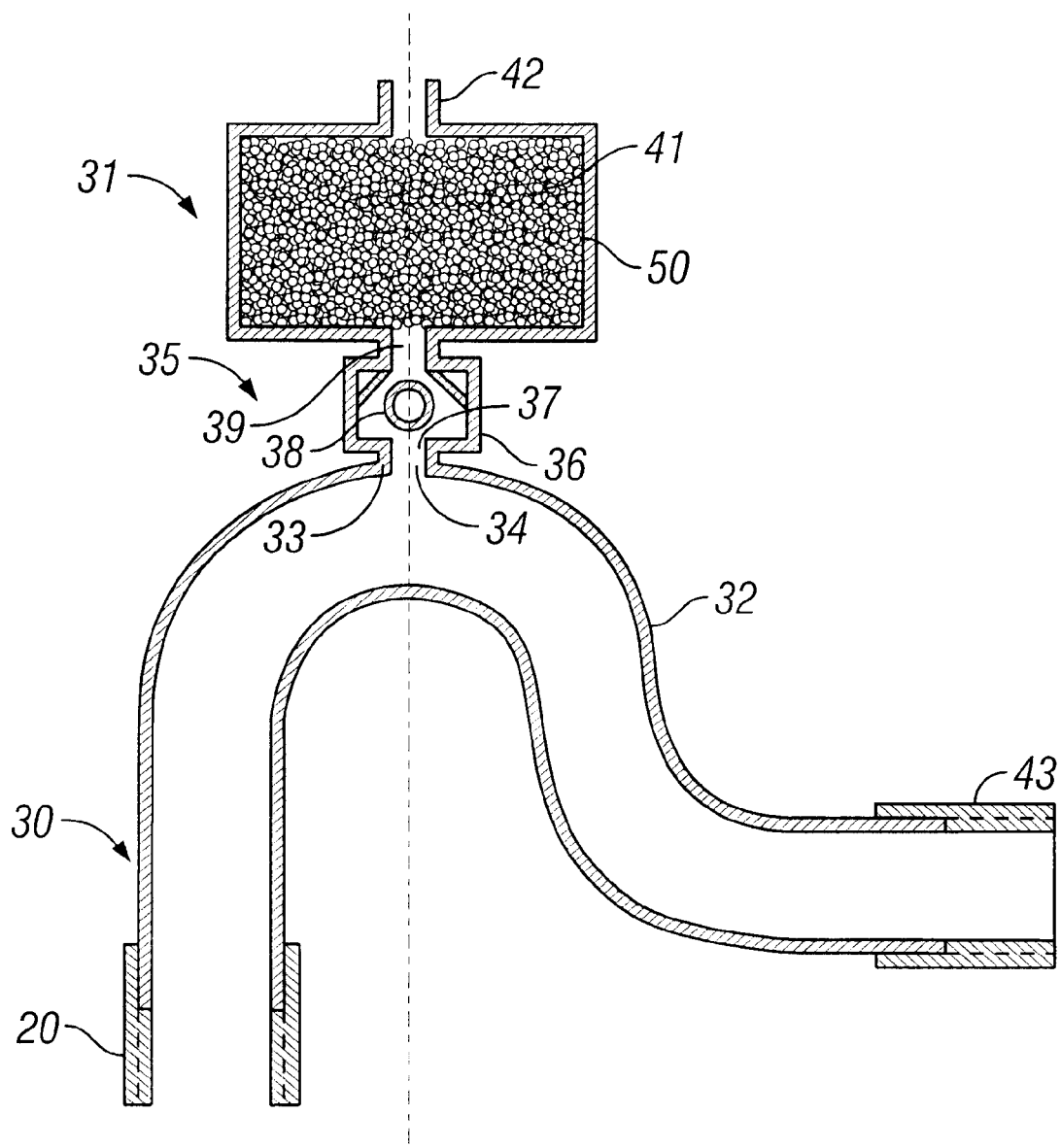
FIG. 2 depicts a cross-sectional view of a gas separator and neutralization device according to the invention.

The invention is being explained in detail by means of an example showing embodiments of the degermination device (FIG. 1) and the gas separator with activated charcoal container (FIG. 2). FIG. 1 shows an embodiment of the degermination device (1). The device (1) comprises a casing (2) in which the UV radiator (3) is arranged and a tube (4) for carrying the fluid. The casing (2) comprises a tube piece (5) with two cover plates—an upper plate (6) and a lower plate (7). Plates (6) and (7) are flanges which fit, in tube piece (5) and, at their exterior foredges, (8) are equipped with a washer (9). The fixation of the cover plates (6) and (7) at tube piece (5) can be effected appropriately e.g. through a screwed joints.

Disposed within a casing is a UV radiator (3). Preferably several radiators (3) are arranged within the perimeter of tube piece (5) in order to achieve the utmost degermnination effect of radiator (3) regarding the fluid running through tube (4). The electric connector (10) for the radiator (3) is led fluid tight through the lower cover plate (7) by means of a screw joint (11). The screw joint (11) consists of a connecting piece (12) arranged in cover plate (7) with a thread pocket (13) placing a washer (14) and compressed with a screw (15) for fluid tight sealing of the electric connector (10).

The tube (4) at its ends (16) and (17) is framed through screw joints (18) with washers and through lower and upper bushings (19) and (20) connected to the cover plates (6) and (7). The fluid runs through tube (4) from bottom to top as indicated with arrow (21).

The lower cover plate (7) contains an inlet nozzle (22) through which fresh air from a pump (here not shown in detail) is fed into the interior space of the casing (23). The air is filtered in order to prevent contamination of the interior space (23) of casing (2), which would otherwise suffer from reduced radiator performance.

The wave length of the light emitted by the radiator (3) is controlled such that(23) ozone is being produced from the air in the interior space. The ozone gathers in the upper part of the interior space (23) near the mouth (24) of an intake tube (25). The intake tube (25) leads to an inlet nozzle (26) of the lowest bushing (19). The produced ozone is added to the streaming fluid in tube (4) through the intake tube (25) and the inlet nozzle (26). The over pressure in the casing (2) produced by the feed air pump effects the admixture. A clack valve (27) is used to avoid a non-desired back-flow through the intake tube (25). At the inlet nozzles (26) a perforated piece of tube (29) closed at its end is put to support the admixture by bubbling the ozone not the fluid.

In the upper cover plate (6) a glass lense (28) is fixed to allow viewing of the interior space to observe the efficiency of the radiator (3).

Also likely already mentioned in connection with the previous registered utility models of the applicant, the present invention can be equipped with further appliances to monitor the effectiveness of the degennination process.

FIG. 2 represents a cross-section of a gas separator (3) and a gas neutralizer (31). The tube bend (32) is screwed into the outlet nozzle of the tube (4). The curvature of the tube bend (32) points to the top. Its vertex (33) contains an opening (34) through which the gases gathering in the tube curvature can escape. Annexed to the opening (34) is a fluid stop valve (35) which comprises a casing (36) with inlet opening (37) when in its lower position. With increasing gas pressure in the tube bend (32) the ball (38) is lifted and the gas can escape through the valve (35). Through opening (39) the gas passes into the connected container with activated charcoal (4) which as its name already indicates is filled with activated charcoal (41). The activated charcoal (41) neutralizes the gases before the gases pass through container exit (92) to the ambient air. In case the fluid and not the gases gets to the opening (37), the lighter ball (38) is lifted by the fluid until it closes the opening (39). Thus, the fluid cannot flow into the container with activated charcoal (40).

At its discharge end (43), the tube bend (32) is equipped with a screw joint through which it can be connected with the discharge tube.

What is claimed is:

1. A device for degermination of a fluid comprising:
   a tube in which the fluid is passed said tube being permeable to U.V. electromagnetic waves;
   a casing disposed to encase and be coaxial about said tube;
   a lower cover plate disposed between said tube and said casing, said lower cover plate having air tight seals about said tube and about said casing;
   an upper cover plate disposed between said tube and said casing, said upper cover plate having air tight seals about said tube and about said casing;
   a casing inlet nozzle adapted to introduce filtered air through said lower cover plate and into an interior volume between said tube, said casing, said lower cover plate and said upper cover plate;
   at least one UV radiator disposed in said interior volume for irradiating the filtered air in said interior volume and for irradiating said tube so the fluid flowing through said tube is irradiated with UV electromagnetic waves;
   an intake tube entirely disposed in said interior volume for passing ozone produced when the filtered air in said interior volume is irradiated by said UV radiator, said intake tube having an inlet mouth for receiving produced ozone, said inlet mouth being disposed in an area of said interior volume adjacent said upper cover plate, said intake tube including a back-up valve, and said intake tube extending into said tube with an outlet nozzle disposed inside said tube to be in communication with the fluid in said tube for introducing ozone to the fluid as the fluid passes into said tube; and
   air pressure for the filtered air in said interior volume being greater than fluid pressure of the fluid passing through said tube.

2. The device of claim 1, further comprising;
   a gas separator in fluid communication with an outlet of said tube, said gas separator including both a tube bend and a fluid stop valve disposed at a vertex of said tube bend; and
   a gas neutralizer in fluid communication with said gas separator, said gas neutralizer including a container of activated charcoal.

3. The device of claim 1, wherein said UV electromagnetic waves have a wavelength of less than 200 nm.

4. The device of claim 1, wherein said UV electromagnetic waves have a wavelength of less than 180 nm.

5. The device of claim 1, wherein said UV electromagnetic waves have a wavelength of both about 254.7 nm and less than 200 nm.

6. The device of claim 1, wherein said UV electromagnetic waves have a wavelength of both about 254.7 nm and less than 180 nm.

7. The device of claim 1, wherein said tube comprises a material selected from the group consisting of quartz glass and UV-resisting/UV-permeable plastic.

8. The device of claim 1, wherein said casing has an inner surface disposed in said interior volume, said inner surface comprising a material selected from the group consisting of aluminum, polished aluminum, and metal oxide.

* * * * *